US006750374B2

(12) United States Patent
Sanderson et al.

(10) Patent No.: US 6,750,374 B2
(45) Date of Patent: Jun. 15, 2004

(54) MANUFACTURE OF CYCLOHEXANE FROM BENZENE AND A HYDROGEN SOURCE CONTAINING IMPURITIES

(75) Inventors: John Ronald Sanderson, Austin, TX (US); Terry Lee Renken, Austin, TX (US); Michael Wayne McKinney, Cedar Park, TX (US)

(73) Assignee: Huntsman Petrochemical Corporation, Austin, TX (US)

( * ) Notice: Subject to any disclaimer, the term of this patent is extended or adjusted under 35 U.S.C. 154(b) by 0 days.

(21) Appl. No.: 10/223,980

(22) Filed: Aug. 20, 2002

(65) Prior Publication Data

US 2003/0114723 A1 Jun. 19, 2003

Related U.S. Application Data

(63) Continuation-in-part of application No. 09/597,313, filed on Jun. 20, 2000, now abandoned.
(60) Provisional application No. 60/148,166, filed on Aug. 10, 1999.

(51) Int. Cl.$^7$ ................................................. C07C 5/10
(52) U.S. Cl. ....................................... 585/267; 585/270
(58) Field of Search ................................. 585/270, 267

(56) References Cited

U.S. PATENT DOCUMENTS

| 2,106,735 | A | | 2/1938 | Gwynn .......................... 196/24 |
| 3,318,965 | A | | 5/1967 | Hutto et al. .................. 260/667 |
| 3,404,190 | A | | 10/1968 | Proctor, Jr. et al. .......... 260/667 |
| 3,711,566 | A | * | 1/1973 | Estes et al. .................. 585/258 |
| 3,767,719 | A | | 10/1973 | Colvert et al. ............... 260/667 |
| 4,251,672 | A | | 2/1981 | Carter et al. ................. 568/814 |
| 4,626,604 | A | * | 12/1986 | Hiles et al. .................. 568/881 |
| 5,189,233 | A | | 2/1993 | Larkin et al. ................ 585/265 |
| 5,668,293 | A | | 9/1997 | Forestiere et al. ........... 585/269 |
| 5,856,603 | A | | 1/1999 | Rekker et al. ............... 585/270 |

OTHER PUBLICATIONS

Eschard et al., "Benzene and Its Industrial Derivatives," E.G. Hancock (Ed.), New York: John Wiley & Sons, pp. 219–237 (1975).
"Ency. Chem. Tech.," vol. 12, pp. 931–937, New York: John Wiley & Sons (1980).
Chou et al., "Benzene Hydrogenation over Supported and Unsupported Palladium," Journal of Catalysis, vol. 107, pp. 129–139 (1987).
Stanislaus et al., "Aromatic Hydrogenation Catalysis: A Review," Catal. Rev.–Sci. Eng., vol. 36(1), pp. 75–123 (1994).

* cited by examiner

Primary Examiner—Thuan D Dang
(74) Attorney, Agent, or Firm—Gardere Wynne Sewell LLP

(57) ABSTRACT

A process for producing cyclohexane by benzene hydrogenation using a hydrogen source that contains impurities, such as carbon monoxide and/or light hydrocarbons, wherein a supported catalyst reduces benzene to cyclohexane and carbon monoxide to methane and water. Alkenes, such as ethylene, are also reduced to their alkane counterparts. Under the disclosed operating conditions, the process proceeds without deactivation of the catalyst, and without the formation of a significant amount of cracking products, such as methylcyclopentane.

20 Claims, No Drawings

MANUFACTURE OF CYCLOHEXANE FROM BENZENE AND A HYDROGEN SOURCE CONTAINING IMPURITIES

CROSS REFERENCE TO RELATED APPLICATIONS

This continuation-in-part application claims the benefit of U.S. Nonprovisional application Ser. No. 09/597,313, filed on Jun. 20, 2000 now abandoned, which claims the benefit of U.S. Provisional Application No. 60/148,166, filed on Aug. 10, 1999.

TECHNICAL FIELD

This invention relates to a process for producing cyclohexane by benzene hydrogenation, and, more particularly, to a process for producing cyclohexane by benzene hydrogenation using a hydrogen source that contains impurities.

BACKGROUND OF THE INVENTION

Over the years, researchers have developed numerous processes for manufacturing cyclohexane from the hydrogenation of benzene. For the most part, the majority of these various processes differ from each other in the techniques used to compensate for impurities, found in either the reaction components themselves or that are generated during the hydrogenation process.

For example, U.S. Pat. No. 3,711,566 (Estes et al.) describes a process in which aromatic hydrocarbon feedstocks containing sulfur are hydrogenated using a fluorided-platinum catalyst. Sulfur, a known poison to platinum catalysts, causes rapid deactivation of the catalyst as the hydrogenation process proceeds. Adding fluorine to the catalyst reduces sulfur poisoning; however, this undesirably increases hydrocracking activity that also deactivates the catalyst. Estes et al. inhibited hydrocracking activity by adding extremely small amounts, of carbon monoxide (a poison of metal catalysts itself) to the pure-hydrogen feed stream. This allowed the carbon monoxide to interact with the acidity of the fluorided-catalyst surface and prevent reactions, like hydrocracking, from taking place. Because carbon monoxide can also poison and deactivate the catalyst, care must be exercised in both purifying the hydrogen feed stream and in adding the carbon monoxide to the pure-hydrogen feed stream in order to achieve proper hydrogenation. This type of hydrogenation process therefore appears most useful when the hydrocarbon feedstock contains substantial amounts of sulfur requiring the catalyst to contain fluorine to prevent the sulfur from poisoning the catalyst.

U.S. Pat. No. 4,626,604 (Hiles et al.) describes a process in which hydrogenation occurs in a series of catalytic stages using at least three adiabatic reaction vessels. Because hydrogenation occurs in stages, lower operating temperatures can be used, which in turn reduces the formation of byproducts such as esters that can poison the catalysts and decrease, catalytic activity. However, Hiles et al. requires that the liquid unsaturated aromatic hydrocarbon be vaporized prior to mixing with the hydrogen gas. Portions of the vaporized unsaturated aromatic hydrocarbon are then hydrogenated in each catalytic stage before the saturated hydrocarbon is cooled and condensed back to liquid-form.

Of particular concern in a conventional hydrogenation of benzene process are impurities found in the hydrogen source, because such impurities often deactivate the catalyst used to promote the hydrogenation reaction. Carbon monoxide is one such impurity that can reversibly poison catalysts, like nickel, used in benzene hydrogenation processes. In the poisoning process, carbon monoxide is adsorbed onto the active sites of the nickel catalyst surface, thereby reducing the activity of the catalyst. Depending on the concentration of carbon monoxide in the hydrogen source, the nickel catalyst can rapidly deactivate.

Once the nickel catalyst has deactivated, the catalyst may be regenerated by heating the catalyst at a temperature from about 220° C. to about 260° C. Because this regeneration process may not be completed in the presence of benzene or cyclohexane (the temperatures required for regeneration tend to promote the formation of large quantities of undesirable cracking products), the reactor must be taken off-line before regeneration of the catalyst. Due to the obvious inconvenience associated with taking the reactor off-line, most conventional benzene hydrogenation processes are designed to limit or prevent deactivation of the catalysts.

In order to prevent or limit deactivation of the nickel catalysts commonly used in benzene hydrogenation processes, most conventional processes require that a highly pure hydrogen source be used. Relatively pure hydrogen sources may be obtained from a steam reformer, and such hydrogen streams typically contain about 96 mole % hydrogen, about 4 mole % methane, and less than about 10 ppm of carbon monoxide and other impurities. Even with such low carbon monoxide levels, these hydrogen streams must still often be further purified to reduce the carbon monoxide levels to less than about 1 ppm before use. As such, these hydrogen streams tend to be expensive, yet they are frequently used because no other alternatives have been available.

Less pure sources of hydrogen are available from steam cracking, catalytic reforming, and hydroalkylation. Hydrogen streams obtained from these sources typically contain from about 10 mole % to about 80 mole % hydrogen, with the remainder comprising impurities such as methane, other light hydrocarbons, and/or carbon monoxide. The level of carbon monoxide in hydrogen streams from these sources is often as great as about 5000 ppm, which often prevents the use of these hydrogen sources in conventional benzene hydrogenation processes.

Therefore, what is needed is a process that: (i) promotes the hydrogenation of benzene to cyclohexane that operates using a lower purity, and thereby, a less expensive source of hydrogen; (ii) proceeds without deactivation of the catalyst due to the presence of carbon monoxide or other impurities in the hydrogen source; and (iii) promotes the hydrogenation of benzene without contributing to the formation of a significant amount of cracking products, such as methylcyclopentane.

SUMMARY OF THE INVENTION

The present invention, accordingly, provides for a process of producing cyclohexane by benzene hydrogenation using a hydrogen source that contains impurities. The supported catalysts used in the present invention reduce benzene to cyclohexane, and reduce carbon monoxide to methane and water. Alkenes, such as ethylene, are also reduced to their alkane counterparts. An advantage of the present invention is that the catalysts used in the disclosed process, if used under the reaction conditions disclosed, do not deactivate in the presence of carbon monoxide or other impurities typically found in hydrogen sources. Another advantage is that the disclosed process proceeds without the formation of a significant amount of cracking products, such as methylcyclopentane.

DETAILED DESCRIPTION OF THE PREFERRED EMBODIMENT

The present invention provides for a process for causing the simultaneous production of cyclohexane from the hydrogenation of benzene and chemical reduction of certain impurities that may be present in the reactants. The process involves providing a first stream comprising benzene; providing a second stream comprising hydrogen and impurities; mixing the first and the second streams to form a reactive mixture; and contacting the reactive mixture with a catalyst to effectuate the reduction of the benzene and impurities. Under the preferred reaction conditions of the present invention, the catalyst will not deactivate rapidly, high benzene and hydrogen conversions will be obtained, and cracking product formation will be held within acceptable limits.

The hydrogen stream used in the process of the present invention may be obtained from a variety of sources, including, but not limited to, steam cracking, catalytic reforming, and/or hydroalkylation. Preferably, the hydrogen source should contain no more than about 15 mole % of impurities, such as, but not limited to, carbon monoxide or light hydrocarbons. More preferably, the hydrogen source should contain no more than about 5 mole % of carbon monoxide and about 10 mole % of light hydrocarbons. The light hydrocarbons may comprise alkanes and/or alkenes with from about one to about three carbon atoms, including, but not limited to, methane and/or ethylene.

The benzene stream may be obtained from any number of sources, including, but not limited to hydrodealkylation, pyrolysis, catalytic reforming or fractional distillation.

The catalysts used in the process of the present invention may be prepared according to any suitable technique known in the art. Typically, the catalyst comprises nickel and copper. The catalyst may also optionally comprise chromium, manganese, iron, cobalt, zinc, molybdenum, tin, or combinations thereof. Preferably, the catalyst comprises from about 15 weight % to about 35 weight % nickel, from about 1 weight % to about 15 weight % copper, and from about 0 weight % to about 5 weight % chromium, manganese, iron, cobalt, zinc, molybdenum, tin, or mixtures thereof. More preferably, the catalyst comprises from about 22 weight % to about 28 weight % nickel, from about 2 weight % to about 6 weight % copper, and from about 0 weight % to about 3 weight % chromium, manganese, iron, cobalt, zinc, molybdenum, tin, or mixtures thereof The support for the catalyst may comprise any material suitable for a support. Preferably, the support comprises either alumina or silica.

Surprisingly, the catalysts used in the process of the present invention do not lose catalytic activity in the presence of impurities, including carbon monoxide, that are contained in the hydrogen source. Nickel catalysts are notoriously well known in the art to be poisoned by carbon monoxide, as discussed above. The process of the present invention prevents this poisoning while reducing benzene to cyclohexane at sufficient rates. Also surprisingly, the catalysts not only function to reduce benzene to cyclohexane, but also reduce carbon monoxide to methane and water, and alkenes, such as ethylene, to their alkane counterparts. Unexpectedly, the reduction of benzene and the impurities proceeds with minimal formation of cracking products, such as methylcyclopentane, even at increased temperatures.

In order to practice the process of the present invention, any suitable reaction vessel may be used. Preferably, the reaction vessel is a reactor. More preferably, the reaction vessel is a jacketed, stainless steel, tubular reactor.

The process of the present invention should be conducted under conditions sufficient to promote the reduction of benzene and the impurities in the reactive mixture. It will be understood by those skilled in the art that conditions of temperature and pressure may vary depending on other variables such as the desired conversion, benzene concentration, hydrogen concentration, carbon monoxide concentration, catalyst particle size, catalyst composition, the heating/cooling efficiency of the reactor system, etc.

Generally, during operation, the exotherm or hot spot temperature in the reactor should be maintained above about 160° C. Preferably, the exotherm or hot spot temperature in the reactor should be maintained from about 160° C. to about 340° C. More preferably, the exotherm or hot spot temperature in the reactor should be maintained from about 190° C. to about 280° C.

Generally, the reactor pressure should be maintained above about 50 psig. Preferably, the reactor pressure should be maintained from about 250 psig to about 2500 psig, and more preferably, from about 400 psig to about 800 psig.

In the process of the present invention, it is preferable to use an excess of benzene, relative to the amount of hydrogen. Under such conditions, the process should be used in, a "front-end" reactor (ie. where the reactor is the first reactor in a series of reactors). The resulting product may then be "finished off" (ie. the benzene levels may be reduced to ppm levels) by a subsequent reactor.

The final cyclohexane product can be collected by separation means generally used in separating liquids such as distillation, centrifugation, density differences or chromatography.

While it is the preferred method to use an excess of benzene in carrying out the process of the present invention, it would be obvious to one skilled in the art that an excess of impure hydrogen, relative to the amount of benzene, could also be used with the catalysts and conditions disclosed in the present invention.

The following examples are illustrative of the present invention, and are not intended to limit the scope of the invention in any way.

Catalyst A (Comparative)

Catalyst A is a conventional, highly active nickel on silica catalyst, available from the Engelhard Corporation, Beachwood, Ohio, under the name Ni-5256 E 3/64. It contains 57% nickel, has a surface area of 260 m$^2$/g, a total pore volume of 0.5 cc/g, and was in the form of 3/64 inch diameter extrusions. Before use, the catalyst was reduced and stabilized. This catalyst is recommended by the supplier for use in benzene hydrogenation processes.

Catalyst B

Catalyst B is a 24% nickel and 4.5% copper catalyst on an alumina support. It was prepared using the standard technique of impregnation of a formed alumina support (1/16 inch extrusion, surface area 100 m$^2$/g) with an aqueous solution of nickel and copper nitrates. The wet impregnated support was dried in an oven to remove the water, and then calcined at about 400° C. to decompose the nitrates to the corresponding nickel and copper oxides. The catalyst precursor was then "activated" by reaction with hydrogen, at temperature of about 300° C. Following activation, the catalyst was stabilized to air with dilute oxygen, at a low temperature. The final catalyst had a surface area of 68 m$^2$/g, and a pore volume of 0.40 cc/g.

Catalyst C

Catalyst C was prepared by co-precipitating a mixture of nickel, copper, and chromium carbonates from an aqueous solution of the mixed metal nitrates and sodium carbonate. The precipitated mixture was then washed with fresh water, dried, and then calcined to produce an oxide powder. The oxide powder was then compounded with fine gamma alumina powder, and the resulting product was formed into $\frac{1}{16}$ inch diameter extrusions. The extrusions were then dried, calcined, activated by reaction with hydrogen, and then stabilized to air by partial reoxidation with air under controlled conditions. The catalyst contained 26.3% nickel, 3.9% copper, and 0.92% chromium. The catalyst had a surface area 209 $m^2/g$, and a pore volume of 0.46 cc/g.

Hydrogenation

The reactor was a Dowtherm-jacketed 1.338"×30" stainless-steel tube equipped with a ¼" thermowell running up through the center of the tube. For each run, the reactor was filled with 250-mL of a catalyst (either catalyst A, B, or C), with glass beads added at the top and bottom of the catalyst.

Liquid benzene (20 wt. %)/cyclohexane (80 wt. %) and gaseous hydrogen (25 mole %)/ methane (75 mole %), with and without various impurities, were fed into the reactor through a static mixer. The reactor pressure was maintained at about 500 psig by means of a backpressure regulator. Both liquid and gaseous samples were collected in stainless-steel bombs and analyzed by a gas chromatograph.

EXAMPLE 1 (COMPARATIVE)

Catalyst A was charged to the reactor, and cyclohexane (80 wt. %)/benzene (20 wt. %) was pumped through the reactor at about 500 g per hour. Methylcyclopentane (60ppm) was present in the liquid feed. Hydrogen (25 mole %)/methane (75 mole %) was fed into the reactor at such a rate that benzene was always in molar excess, relative to the hydrogen (approximately 75 to 85 benzene conversion at 100% hydrogen conversion). No carbon monoxide was present in the hydrogen/methane feed. The following results were obtained:

TABLE I

| Dowtherm Temp. (° C.) | Hot Spot Temp. (° C.) | Hydrogen Conversion (%) | Benzene Conversion (%) | Methylcyclo-pentane (ppm) |
|---|---|---|---|---|
| 100 | 158 | 99.7 | 86.8 | 60 |
| 120 | 171 | 99.6 | 83.5 | 90 |
| 140 | 191 | 99.4 | 87.3 | 250 |

The results of this example show that catalyst A is highly operable when carbon monoxide is not in the hydrogen/methane feed. This result is expected because this catalyst is commercially sold for use in benzene hydrogenation processes.

EXAMPLE 2 (COMPARATIVE)

A was charged to the reactor, and cyclohexane (80 wt. %)/benzene (20 wt. %) was pumped through the reactor at about 500 g per hour. Methylcyclopentane (60 ppm) was present in liquid feed. Hydrogen (25 mole %)/methane (75 mole %) that contained 2000 ppm of carbon monoxide was fed into the reactor at such a rate that benzene was always in molar excess relative to the hydrogen (approximately 75 to 85% benzene conversion, at 100% hydrogen conversion). The following results were obtained:

TABLE II

| Dowtherm Temp. (° C.) | Hot Spot Temp. (° C.) | Hydrogen Conv. (%) | Benzene Conv. (%) | MCP (ppm) | MCP produced (ppm) | Time on-stream (hrs.) |
|---|---|---|---|---|---|---|
| 100 | 144 | 75.2 | 42.1 | 60 | 0 | 1.0 |
| 100 | 106 | 50.0 | 12.9 | 50 | 0 | 7.0 |
| 140 | 206 | 98.9 | 80.1 | 470 | 410 | 21.0 |

The results of this example demonstrate that catalyst A tends to deactivate in the presence of carbon monoxide. After only one hour on-stream, the percent of benzene and hydrogen conversion is significantly below the conversion seen for this catalyst in the absence of carbon monoxide (Example 1). After seven hours on-stream, the percent of hydrogen and benzene conversion drops even more, indicating that the catalyst is undergoing deactivation. Further, at the highest hot spot temperature (i.e. 206° C.), the amount of methylcyclopentane produced is prohibitively high.

EXAMPLE 3

Catalyst B was charged to the reactor, and cyclohexane (80 wt. %)/benzene (20 wt. %) was pumped through the reactor at about 500 g per hour. Methylcyclopentane (110 ppm) was present in the liquid feed. Hydrogen (25 mole %)/methane (75 mole %) was fed into the reactor at such a rate that benzene was always in molar excess relative to the hydrogen (approximately 75 to 85% benzene conversion at 100% hydrogen conversion). No carbon monoxide was present in the hydrogen/methane feed. The following results were obtained:

TABLE III

| Dowtherm Temp. (° C.) | Hot Spot Temp. (° C.) | Hydrogen Conversion (%) | Benzene Conversion (%) | Methylcyclo-pentane (ppm) |
|---|---|---|---|---|
| 120 | 162 | 99.1 | 83.3 | 60 |
| 140 | 182 | 99.7 | 83.8 | 90 |
| 160 | 189 | 99.7 | 84.0 | 250 |
| 180 | 216 | 99.6 | 83.6 | 420 |

The results of this example demonstrate that catalyst B is highly operable in the absence of carbon monoxide in the hydrogen/methane feed.

EXAMPLE 4

Catalyst B was charged to the reactor, and cyclohexane (80 wt. %)/benzene (20 wt. %) was pumped through the reactor at about 500 g per hour. Methylcyclopentane (110 ppm) was present in the liquid feed. Hydrogen (25 mole %)/methane (75 mole %) that contained 2000 ppm of carbon monoxide was fed into the reactor at such a rate that benzene was always in molar excess relative to the hydrogen (approximately 75 to 85% benzene conversion at 100% hydrogen conversion). The following results were obtained:

TABLE IV

| Downtherm Temp. (° C.) | Hot Spot Temp. (° C.) | Hydrogen Conv. (%) | Benzene Conv. (%) | MCP (ppm) | MCP produced (ppm) | Time on-stream (hrs.) |
|---|---|---|---|---|---|---|
| 158 | 184 | 100 | 84.3 | 170 | 60 | 1.0 |
| 171 | 204 | 100 | 82.5 | 310 | 200 | 15 |
| 170 | 183 | 100 | 81.1 | 230 | 120 | 32 |

The results of this example show that catalyst B does not deactivate, and remains operable even in the presence of carbon monoxide in the hydrogen/methane feed. Even after 32 hours on-stream, hydrogen conversion remains at 100%, and benzene conversion only drops slightly. While the levels of methylcyclopentane slightly increase over-time, and with increasing hot spot temperatures, the methylcyclopentane levels are still within acceptable limits.

EXAMPLE 5

Catalyst B was charged to the reactor, and cyclohexane (80 wt. %)/benzene (20 wt. %) was pumped through the reactor at about 500 g per hour. Methylcyclopentane (60 ppm) was present in the liquid feed. Hydrogen (25 mole %)/methane (75 mole %)/ethylene (1.5 mole %) that contained 2000 ppm of carbon monoxide was fed into the reactor at such a rate that benzene was always in molar excess relative to the hydrogen (approximately 75 to 85% benzene conversion at 100% hydrogen conversion). The following results were obtained:

TABLE V

| Downtherm Temp. (° C.) | Hot Spot Temp. (° C.) | Hydrogen Conversion (%) | Benzene Conversion (%) | Methylcyclo-pentane (ppm) | Ethane (Mol %) |
|---|---|---|---|---|---|
| 120 | 162 | 98.1 | 80.0 | 70 | 1.73 |
| 140 | 184 | 98.2 | 83.4 | 100 | 1.77 |
| 160 | 203 | 98.0 | 85.6 | 280 | 1.80 |

The results of this example demonstrate that the addition of ethylene to the hydrogen/methane/carbon monoxide feed does not adversely affect the activity of catalyst B. As the results show, catalyst B is capable of quantitatively converting ethylene in the hydrogen/methane/carbon monoxide feed to ethane, while at the same time, the catalyst continues to promote high hydrogen and benzene conversion, as well as minimal methylcyclopentane production.

EXAMPLE 6

Catalyst C was charged to the reactor, and cyclohexane (80 wt. %)/benzene (20 wt. %) was pumped through the reactor at about 500 g per hour. Methylcyclopentane (110 ppm) was present in the liquid feed. Hydrogen (25 mole %)/methane (75 mole %) was fed into the reactor at such a rate that benzene was always in molar excess relative to the hydrogen (75 to 85% benzene conversion at 100% hydrogen conversion). No carbon monoxide was present in the hydrogen/methane feed. The following results were obtained:

TABLE VI

| Downtherm Temperature (° C.) | Hot Spot Temperature (° C.) | Hydrogen Conversion (%) | Benzene Conversion (%) | Methylcyclo-pentane (ppm) |
|---|---|---|---|---|
| 160 | 209 | 99.2 | 87.5 | 190 |
| 140 | 184 | 99.4 | 85.2 | 100 |

The results of this example demonstrate that catalyst C is operable in the absence of carbon monoxide in the hydrogen/methane feed.

EXAMPLE 7

Catalyst C was charged to the reactor, and cyclohexane (80 wt. %)/benzene (20 wt. %) was pumped through the reactor at about 500 g per hour. Methylcyclopentane (110 ppm) was present in the liquid feed. Hydrogen (25 mole %)/methane (75 mole %) that contained 2000 ppm carbon monoxide was fed into the reactor at such a rate that benzene was always in molar excess relative to the hydrogen (75 to 85% benzene conversion at 100% hydrogen conversion). The following results were obtained:

TABLE VII

| Downtherm Temperature (° C.) | Hot Spot Temperature (° C.) | Hydrogen Conversion (%) | Benzene Conversion (%) | Methylcyclo-pentane (ppm) |
|---|---|---|---|---|
| 156 | 247 | 82.6 | 58.7 | 780 |
| 156 | 197 | 97.7 | 77.4 | 170 |
| 165 | 198 | 98.1 | 77.7 | 160 |
| 178 | 218 | 98.9 | 75.5 | 260 |

The results of this example demonstrate that catalyst C promotes high hydrogen and benzene conversion, as well as minimal methylcyclopentane production when the hot spot temperature is below about 247° C. At a temperature of about 247° C., catalyst C tends to show reduced hydrogen and benzene conversion, as well as higher levels of methylcyclopentane production. This result tends to indicate that a hot spot temperature of 247° C. is somewhat above the desired hot spot temperature for catalyst C.

Although illustrative embodiments have been shown and described, a wide range of modification, changes, and substitution is contemplated in the foregoing disclosure. In some instances, some features of the disclosed embodiments may be employed without a corresponding use of the other features. Accordingly, it is appropriate that the appended claims be construed broadly and in a manner consistent with the scope of the invention.

What is claimed is:

1. A process for producing cyclohexane from benzene which comprises the steps of:
   a) providing a first stream comprising benzene;
   b) providing a second stream which is predominantly hydrogen and also comprises carbon monoxide;
   c) mixing the first and the second streams to form a reactive mixture;
   d) contacting the reactive mixture with a catalyst comprising nickel, copper, and at least one other element selected from the group consisting of: chromium, manganese, iron, cobalt, zinc, molybdenum, tin, and mixtures thereof, so as to provide a reaction product mixture; and
   e) recovering cyclohexane from the reaction product mixture, to provide a cyclohexane product.

2. A process according to claim 1 wherein the content of carbon monoxide in the second stream is any amount between 0.0010% to 1.000% by weight based upon the total weight of the second stream.

3. A process according to claim 1 wherein the content of cyclohexane in the reaction product mixture is any amount in the range between 20.00% and 99.99% by weight based upon the total weight of the reaction product mixture.

4. A process according to claim 1 wherein a methylcyclopentane content in the cyclohexane product is less than 300 parts per million by weight based upon the total weight of the cyclohexane.

5. A process according to claim 1 wherein the cyclohexane product is recovered by distillation.

6. A process according to claim 1 in which benzene is present in the first stream in an amount of between 20% and 100% by weight based upon the total weight of the first stream.

7. A process according to claim 1 wherein the reactive mixture is maintained at any temperature in the range of between 100° C. and 340° C.

8. A process according to claim 1 wherein the reactive mixture is maintained at any pressure in the range of between 50 psig and 2500 psig.

9. A process according to claim 1 wherein the nickel content of the catalyst is any amount between 15.00% and 35.00 percent by weight, including every hundredth percentage therebetween.

10. A process according to claim 1 wherein the copper content of the catalyst is any amount between 1.00% and 15.00% percent by weight based upon the total weight of the catalyst, including every hundredth percentage therebetween.

11. A process according to claim 1 wherein chromium is present in the catalyst in any amount between 0.10% and 5.00% percent by weight based upon the total weight of the catalyst, including every hundredth percentage therebetween.

12. A process according to claim 1 wherein the catalyst is a supported catalyst and is supported on a support material selected from the group consisting of: silica and alumina.

13. A process according to claim 1 wherein the molar quantity of benzene in the reactive mixture is greater than the molar quantity of hydrogen in the reactive mixture.

14. A process according to claim 1 wherein the molar quantity of hydrogen in the reactive mixture is greater than the molar quantity of benzene in the reactive mixture.

15. A process for the hydrogenation of benzene comprising:
   a) providing a first stream comprising benzene;
   b) providing a second stream that is predominantly hydrogen and further comprises carbon monoxide;
   c) charging a reaction vessel with a catalyst comprising nickel, copper, and at least one other element selected from the group consisting of: chromium, manganese, iron, cobalt, zinc, molybedenum, tin, and mixtures thereof;
   d) mixing the first and second streams to form a reactive mixture;
   e) feeding the reactive mixture to the reaction vessel so that the reactive mixture contacts the catalyst to provide a reaction product mixture; and
   f) recovering cyclohexane from the reaction product mixture, to provide a cyclohexane product.

16. A process according to claim 15 wherein the second stream further comprises light hydrocarbons having about one to about three carbon atoms.

17. A process according to claim 15 wherein the reactive mixture is maintained at a temperature of about 100° C. to about 340° C.

18. A process according to claim 15 wherein the reactive mixture is maintained at a pressure of about 50 psig to about 2500 psig.

19. A process according to claim 15 wherein the reaction vessel is a reactor and mixing of the first stream and the second stream is accomplished in a static mixer.

20. A process according to claim 15 wherein the cyclohexane product is recovered by separation means.

* * * * *